(12) United States Patent
Go Boncan et al.

(10) Patent No.: US 6,817,238 B2
(45) Date of Patent: Nov. 16, 2004

(54) CEMENT EXPANSION/CONTRACTION TEST APPARATUS

(75) Inventors: Virgilio C. Go Boncan, Spring, TX (US); W. Scott Bray, Cypress, TX (US)

(73) Assignee: BJ Services Company, Houston, TX (US)

(*) Notice: Subject to any disclaimer, the term of this patent is extended or adjusted under 35 U.S.C. 154(b) by 0 days.

(21) Appl. No.: 10/177,742

(22) Filed: Jun. 21, 2002

(65) Prior Publication Data

US 2003/0033893 A1 Feb. 20, 2003

Related U.S. Application Data (60) Provisional application No. 60/300,202, filed on Jun. 22, 2001.

(51) Int. Cl.[7] .......................... G01F 17/00; G01N 19/00; G01N 33/38
(52) U.S. Cl. .......................... 73/149; 73/429; 73/865.6; 73/866
(58) Field of Search .......................... 73/149, 429, 865.6, 73/864.53–864.55, 866, 803; 249/66.1, 67, 82, 117, 126, 155, 158, 163, 165; 264/140.4, 40.5, 40.7, 288; 374/55, 56

(56) References Cited

U.S. PATENT DOCUMENTS

| | | | | |
|---|---|---|---|---|
| 2,978,781 A | * | 4/1961 | Shuman | 425/150 |
| 3,239,880 A | * | 3/1966 | Oxel | 374/55 |
| 3,574,281 A | * | 4/1971 | Casey et al. | 374/55 |
| 3,619,463 A | * | 11/1971 | Budin et al. | 373/119 |
| 3,779,085 A | * | 12/1973 | Rice | 73/866 |
| 4,408,489 A | * | 10/1983 | Spangle | 73/866 |
| 4,446,920 A | * | 5/1984 | Woytek et al. | 166/297 |
| 4,491,017 A | * | 1/1985 | Iyer | 73/865.8 |
| 4,934,180 A | * | 6/1990 | Hulsman | 73/49.3 |
| 4,970,464 A | * | 11/1990 | Williams | 324/207.13 |
| 5,009,512 A | * | 4/1991 | Lessi et al. | 374/6 |
| 5,105,885 A | * | 4/1992 | Bray et al. | 166/279 |
| 5,336,316 A | * | 8/1994 | Dawson et al. | 106/724 |
| 5,487,307 A | * | 1/1996 | Landgren et al. | 73/803 |
| 5,741,971 A | * | 4/1998 | Lacy | 73/597 |
| 6,527,438 B2 | * | 3/2003 | Zollinger et al. | 374/56 |

OTHER PUBLICATIONS

Buntoro et al., "The effect of Neat Magnesium Oxide (MgO) as Expanding Addititive on Cement Shear Bond Strength at High Temperature Up To 2500C", Proceedings World Geothermal Congress 2000, Jun. 2000, pp 2325–2333.*

"Chemical Shrinkage Properties of Oilfield Cements"; M.E. Chenevert, SPE, and B.K. Shrestha, SPE, U. of Texas; Copyright 1991 Society of Petroleum Engineers (pp. 37–43).

(List continued on next page.)

*Primary Examiner*—Hezron Williams
*Assistant Examiner*—David A. Rogers
(74) *Attorney, Agent, or Firm*—Howrey Simon Arnold & White, LLP (57) ABSTRACT

An apparatus for measuring volumetric changes in cement as the cement is exposed to pressures and temperatures to simulate down-hole conditions, in a high-pressure high-temperature chamber is described. The apparatus is described as a mold having a first section adjacent a base and a second section movably attached to the first section and adjacent the base in which cement may be placed. The apparatus includes a sensor to measure the movement of the first and second sections relative to one another in response to volumetric changes in the cement. Also described is a method of measuring the volumetric changes in cement as the cement is exposed to simulated down-hole pressures and temperatures in a high-pressure, high-temperature chamber.

51 Claims, 7 Drawing Sheets

OTHER PUBLICATIONS

"Expansive and Shrinkage Characteristics of Cements Under Actual Well Conditions," JPT (Aug. 1973) 905–909; Beirute, R. and Tragesser, A.

"True Expansive Characteristics of Commercially Available Expansive Cement Under Actual Well Conditions," paper SPE 6013 presented at the 1976 SPE Annual Technical Conference and Exhibition, New Orleans, Oct. 3–6; Beirute, R.M.

"CaO– and/or MgO–Swelling Cements: A Key for Providing a Better Annualar Sealing?"; Reza Ghofrani and Helko Plack, Inst. for Tlefbohrtechnik, Technical U. Clausthal; SPE/IADC 25697 (pp. 199–214).

"Standard Practice for Use of Apparatus for the Determination of Length Change of Hardened Cement Paste, Mortar, and Concrete"; ASTM Designation: C490–93a (pp. 265–269).

* cited by examiner

FIG. 10

CEMENT EXPANSION/CONTRACTION TEST APPARATUS

CROSS REFERENCE TO RELATED APPLICATIONS

This application claims priority to the Provisional Application No. 60/300,202, entitled "Cement Expansion/Contraction Test Apparatus," filed Jun. 22, 2001.

BACKGROUND OF THE INVENTION

1. Field of the Invention

The invention relates to an apparatus and method for use in the measurement of fluids used in the field of oil and gas recovery. More particularly, this invention relates to an apparatus such as a mold adapted to detect the expansion or shrinkage of cement as the cement is exposed to simulated down-hole conditions, such as high-pressure, high-temperature applications. A method for measuring the expansion or shrinkage of the cement is also disclosed.

2. Description of the Related Art

It is a fact that cement will undergo chemical shrinkage when it sets. The chemical shrinkage—or the hydration volume reduction (HVR)—of a cement slurry is a direct result of water chemically reacting with the cement clinker crystalline materials forming calcium silicate crystals. The chemical shrinkage of the slurry can be substantial, e.g. seven percent of its original volume, depending on the slurry formulation. The matrix volume change of the cement slurry can lead to poor cement bonding or to the creation of micro-annuli. These micro-channels or poorly bonded areas may allow well fluids like gas, oil, steam, water, and/or the combination of fluids to migrate to the surface or to other zones of the well. The migration of well fluids will result in lower production revenue. Additionally, the migration of well fluids can increase well maintenance costs, increase casing corrosion, and reduce the life of the well. The formation of micro-annuli may require a secondary cement job or squeeze cementing, thus increasing the total well cost. The migration of well fluids can also lead to complete loss of the well due to blowout. In injection wells, the poor cement bonding can lead to a higher injection cost and lower well efficiency. These well fluids can migrate, contaminate, and pollute fresh water aquifers.

It is uncommon for oil and gas well service companies to evaluate, test or measure this important cement property. This is due primarily to a lack of the appropriate efficient and accurate equipment to continuously measure the cement shrinkage or expansion while it is curing under humid environment and under down-hole temperature and pressure.

Few methods and ideas have been tested to accurately measure volume change of cement slurry. M. E. Chenevert and B. K. Shrestha from the University of Texas have written a SPE paper on the Chemical Shrinkage Properties of Oilfield Cement. The apparatus used in the experiment consists of a high-pressure cell, a high-pressure injection pump with pressure transducer and digital gauge, a heating jacket, a vacuum pump, autoclave high-pressure tubing and valves, and an electronic thermostat with a sensing thermocouple. For each test, a thin-walled lead tube with a 1.375-inch diameter by 4 inches long is used. The lead tubes containing the slurry is capped and placed inside the high-pressure cell and inside the heating jacket. The high-pressure injection pump is used to inject mineral oil around the test sample and to the control pressure during the test. The desired heat is applied to the test sample with the heating jacket and controlled with the thermostat.

The volumetric property of the slurry is measured directly by the volume of mineral oil injected. Therefore, it is necessary to calibrate the pump and establish the relationship between the volume of oil injected to the positive-displacement pump read-out. During a test, if the temperature of the test cell changes then the pressure will change too. The behavior is due to the thermal expansion or contraction of the mineral oil. Depending on the temperature change, the pressure regulator will activate the pump by removing or adding mineral oil to the system. These can indicate a false reading of cement volumetric changes. Therefore, it is necessary to establish a mineral oil thermal expansion coefficient for each test temperature. The mineral oil correction factor will be used in slurry volumetric calculations.

Other authors, Reza Ghofrani and Heiko Plack, wrote SPE/IADC 25697 ("CaO-and/or MgO-Swelling Cements: A Key for Providing a Better Annular Sealing?"). In their experiment, they use a different apparatus to measure the matrix volume change in cement slurry. The apparatus consists of a test cell, a gear mechanism, a floating piston, potentiometer, autoclave and chart recorder. The test cell is divided into three-sections: 1) a water reservoir; 2) a sample chamber; and 3) a measuring head. A sintered metal disk and a filter paper are mounted at the bottom of the cement sample. Below the metal disk is a cavity filled with water. A metal plug with sealed assembly is used to cap the bottom of the water chamber. The autoclave curing pressure is transmitted to the cement during the test by the way of the metal plug to the water and to the cement. This will allow the cement to absorb additional water as required during the hydration process. On the top of the cement sample is a rubber cup sleeve that seals the cement against the pressurizing fluid (mineral oil). A floating piston is installed on top of the rubber cup sleeve. The axial motion of the piston caused by the changes in the matrix volume is converted to a rotational motion by a gear mechanism. The gear mechanism will alter the position of the pointer across the potentiometer resistor. The shifting position of the pointer across the resistor provides a variation of the voltage signal. The measured voltages along with the autoclave-temperature and pressure are monitored continuously by means of a chart recorder. The matrix volume change is calculated using the calibration chart. The calibration chart is expressed as piston height versus voltage signal reading.

One advantage of the Ghofrani/Plack apparatus is that fresh water is pushed into the cement matrix while curing. The test data from the apparatus can be subjective due to the measuring head design. The rubber cup sleeve that seals the cement against the mineral oil can absorb some of the displacement movement or it can swell to provide a positive movement for the piston. The mechanical tolerances on the gear mechanism can affect equipment performance from one unit to the other. The volumetric change in some slurries may be in the micro-inches spectrum and converting it to axial motion by the piston, to a rotational movement by the gear mechanism, and to electrical signal by the potentiometer. The measuring head design may be impractical for field application accuracy may be sacrifice. Currently, none of these concepts has been built commercially to support the oil well industry.

SUMMARY OF THE INVENTION

An apparatus is described for measuring volumetric changes in cement as the cement is exposed to a given pressure and temperature in a high-pressure high-temperature chamber. In some embodiments, the apparatus has a first section adjacent a base and a second a second section movably attached to the first section, the second section adjacent the base. The first section, the second section, and the base may define a mold into which a measurable amount of cement may be placed. The apparatus may include a sensor that is functionally associated with at least one of the sections. The sensor may be adapted to measure the movement of the first and second sections relative to one another in response to volumetric changes in the cement when the cement is exposed to simulated downhole pressures and temperatures. The apparatus may include a seal between the first and second sections, in some embodiments.

In some embodiments, the apparatus includes a fastening assembly, which may comprise a first bolt surrounded by a first spring and having a threaded end, the first bolt passing through a first hole in the second section and threadedly engaged with a first threaded hole in the first section, and a second bolt surrounded by a second spring and having a threaded end, the second bolt passing through a second hole in the second section and threadedly engaged with a second threaded hole in the first section, the springs adapted to bias the second section into contact with the first section.

In some embodiments, an apparatus is described having a means for moving with volumetric changes in the cement movably attached to the first section, the means for moving adjacent the base. The apparatus may include a sensing means contacting at least one of the sections for measuring the movement of the means for moving in response to volumetric changes in the cement when the cement is exposed to high pressure and high temperature, or a means for sealing.

Also described is a method of measuring volumetric changes in cement as the cement is exposed to a given pressure and temperature in a high-pressure high-temperature chamber utilizing the molds described herein, filling the mold with cement, placing the mold into the high-pressure high-temperature chamber, raising the pressure to a given value and the temperature to a given value, changing the pressure to other given values and the temperature to other given values, and recording data from the sensor over time.

In some aspects, a basket is described which may facilitate the processing of multiple molds at the same time. The basket may include mounting rods, a top plate, and a bottom plate.

While the invention is susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents, and alternatives falling within the spirit and scope of the invention as defined by the appended claims.

DESCRIPTION OF ILLUSTRATIVE EMBODIMENTS

Illustrative embodiments of the invention are described below as they might be employed in volumetric measurements. In the interest of clarity, not all features of an actual implementation are described in this specification. It will of course be appreciated that in the development of any such actual embodiment, numerous-implementation-specific decisions must be made to achieve the developers' specific goals which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments of the invention will become apparent from consideration of the following descriptions and drawings.

In some embodiments, a modified high-pressure high-temperature (HPHT) cement curing chamber 90 is described. The HPHT curing chamber 90 consists of autoclave test cell with heaters, temperature controller, and hydraulic pump with pressure regulator. Thus, the HPHT curing chamber may simulate down hole pressures and temperatures. The expansion/contraction mold 50 is fitted inside the HPHT curing chamber 90. Outside the HPHT curing chamber 90 is a high-pressure spring loaded linear displacement transducer 80 (LDT) with Autoclave fittings. The signal from LDT 80 is processed by the Data Acquisition Unit 82 (DAU) and then the DAU 82 communicates the process signal to a device 84 such as computer or a chart recorder. The computer or the chart recorder will store the data from the test. The equipment will continuously monitor cement expansion, before and after cement hydration process. The equipment will also measure cement shrinkage continuously after the cement has set. Measurements may be taken under a humid environment and under down-hole temperature and pressure. The innovative mold design will allow cement movement or volumetric changes in all three directions ("X", "Y", and "Z" axis). See FIGS. 1, 2, and 3. Using a mold basket 40, the HPHT curing chamber 90 can be fitted to accommodate three molds 50 stacked one on top of the other. Fitted with three LDTs 80 and appropriate electronic accessories, the computer can simultaneously process and store test data from three different cement formulations 10 including test temperature and pressure. Of course, as would be apparent to one of ordinary skill in the art having the benefit of this disclosure, the number of cement formulations 10 and molds 50 is not limited to three; rather, any number of cement formulations 10 could processed in molds 50 by modifying the size and shape of the chamber 90 or molds 50, for example.

Advantages of the apparatus include the following: The sample of cement is not subject to mechanical restriction on the sample, as the mold design allows the cement 10 to expand or shrink in three axes. By way of example, three different slurry formulations 10 can be tested simultaneously at the same bottom-hole temperature and pressure. The apparatus can independently measure the linear expansion or contraction of the three different cement formulations 10. The (HPHT) linear displacement transducer 80 can easily be calibrated with a micrometer. The cement volumetric change is transmitted from the mold body 50, to the LDT 80, and to the computer. A calibrated (HPHT) linear displacement transducer 80 will provide a direct reading of expansion or contraction. There is no need for elaborate mathematical calculations. Confining pressure and temperature will not affect the performance of the LDT 80. Therefore, it will not affect test measurements. It is not necessary to determine or calibrate the coefficient of expansion of the confining fluids. The cement 10 is cured under a humid environment and under down-hole temperature and pressure. Existing HPHT curing chambers 90 can be modified and fitted for the expansion or contraction testing. At the end of the volumetric test, the set cement 10 can be tested for permeability. The modified HPHT curing chamber 90 can still be used for compressive strength testing. No need exists for a different machine or pressurized curing vessel. Further, off-the-shelf software can be used to monitor the test. No need exists to invest on different software. An old 468 computer or higher with Windows 95 can be used to monitor and store the test data.

In some embodiments, a standard cement curing chamber 90 may be modified to accept a high-pressure/high temperature linear distance transducer 80 as disclosed herein. In some embodiments, an expansion/shrinkage mold 50 is fabricated along with the necessary fittings and accessories. An electronic circuit may be assembled to measure, collect, and store the test data in a PC computer.

Test data generated from some embodiments can continuously measure cement expansion or shrinkage accurately under humid conditions and at down-hole temperature and pressure. The design of the mold 50 allows the cement 10 to move freely in three (X, Y and Z) axes while curing at down-hole conditions. In this case, the cement slurry 10 is assumed to expand or shrink uniformly in three axes as long as the slurry is subjected to the same confining conditions. The linear distance transducer 80 will detect any movement directly from two parallel planes inside the mold 50 along the X-axis. Alternatively, three linear distance transducers 80 may be utilized to measure movement in the X, Y, and Z directions.

After assembly of the apparatus, before any testing, the linear distance transducer in conjunction with the electronic data acquisition unit is calibrated accurately using a Venier caliper. Once the calibration of the linear displacement transducer is established, re-calibration is not necessary on the preceding test. Another feature of the invention is the apparatus does not require any complicated calculations to function. The cement slurry 10, mold 50, confining fluids 12, and test cell 92 are exposed to the same test conditions at the same time. Therefore, the coefficient of expansion of the mold 50, confining fluid 12, and test cell 92 does not interfere with the test data. In addition, the slurry 10 is cured under humid condition at down-hole temperature and pressure at all time during the test.

Based on testing (see the attached test data), it has been determined that the cement 10 may continuously change its dimensions several days or more than a week after it has been mixed. In order to maximize the equipment efficiency, it is preferable that a curing chamber 90 is used that will accommodate multiple linear distance transducers 80 at the same time.

Figure 1:
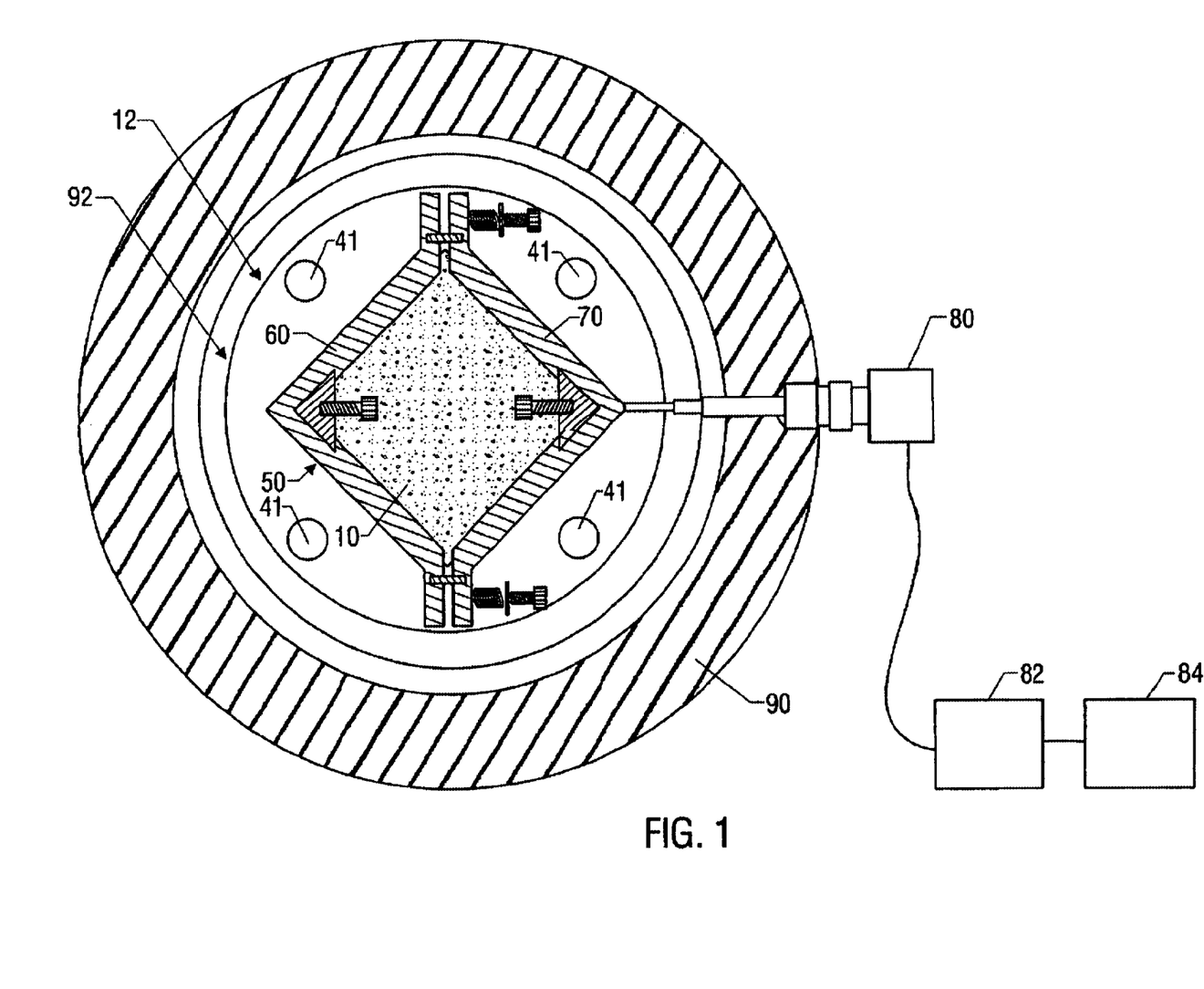
FIG. 1 shows a top view of one embodiment of the present invention having a mold mounted inside a high-pressure high-temperature chamber.

Embodiments of the invention will now be described with reference to the accompanying figures. Referring to FIG. 1, one embodiment of the present invention is shown having a mold 50 inside a high-pressure high-temperature curing chamber 90. High-pressure high-temperature curing chamber 90 is any standard high-pressure high-temperature test cells commercially available, such as Chandler Engineering Curing Vessel model #7-700-5, from Chandler Engineering, Tulsa, Okla. This chamber 90 thus can simulate elevated down-hole pressures and temperatures.

Mold 50 is shown to be comprised of a first section 60 and a second section 70 as described more fully hereinafter. Mold 50 may be filled with cement 10.

Functionally associated with second section 70 is sensor 80. Sensor 80 may be a linear displacement transducer. Sensor 80 may contact second section 70, for example. A standard high-pressure high-temperature curing chamber 90 typically is not equipped with a sensor 80, but can be modified to insert sensor 80. Sensor 80 may be a spring-loaded linear displacement transducer or any other type of linear displacement transducer known by one of ordinary skill in the art having the benefit of this disclosure, such, as an electromagnetic linear displacement transducer. Electrically connected to the linear displacement transducer is a data acquisition unit 82 which collects readings from sensor 80.

Electrically connected to data acquisition unit 82 is a device 84 for storing and displaying the data from the data acquisition unit 82 over time. For example, device 84 may be a computer or a chart recorder.

In FIG. 1, mold 50 is shown in mold basket 40 described more fully herein. In the embodiment shown, the mold 50 includes mounting holes 41 for attaching the molds 50 to a basket 40 as more fully described herein. The mold basket 40 is placed into the high-pressure high-temperature chamber 90. A pressurizing medium 12 is then pumped into the chamber to increase the pressure. This pressurizing medium may be water, or oil, or any other fluid capable of increasing the pressure within the chamber 90 by being pumped into the chamber 90, by a hydraulic pump (not shown) for example. The chamber 90 also includes heaters (not shown) for increasing the temperature within the chamber.

Figure 2:
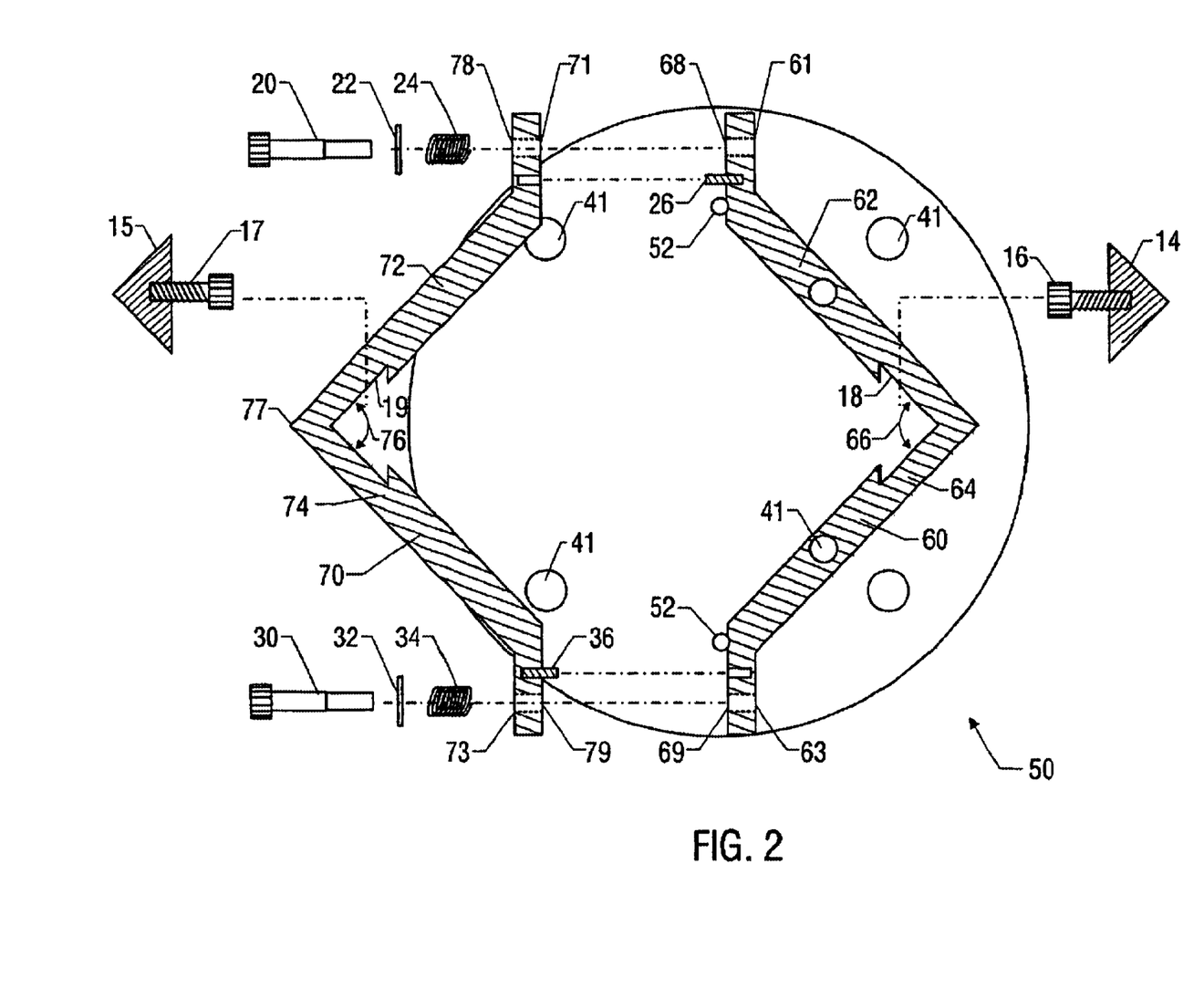
FIG. 2 shows a top view of an exploded view of a mold of one embodiment of the present invention.

As shown in FIG. 2, a seal 52 is placed between the two sections 60 and 70 to prevent the first section 60 and the second section 70 from contacting each other. Seal 52 may be an O-ring, or a low-durometer rubber seal, a thin wall TYGON tubing, or any other type of seal will allow the sections to be compressed together, as described more fully herein, while preventing the cement from leaking out of the sections.

As shown in FIG. 2, first section 60 may be comprised of sides 62 and 64, each of which is substantially straight and form a plane. Sides 62 and 64 meet at an angle 66. In this embodiment, angle 66 is 90 degrees. Further, each of sides 62 and 64 has a mating surface 68 and 69 respectively to mate with the second section 70 as described more fully herein.

Similarly, second section 70 may be comprised of sides 72 and 74, each of which is substantially straight and form a plane. Sides 72 and 74 meet at an angle 76. In this embodiment, angle 76 is 90 degrees. Also shown in FIG. 2 is contact location 77 of the second section 70. Further, each of sides 72 and 74 has a mating surface 78 and 79 respectively to mate with the first section 60 as described more fully herein.

As shown in FIG. 2, in this embodiment, second section 70 is movably attached to the first section 60 by a fastening assembly. The fastening assembly in this embodiment is comprised as follows. A first bolt 20 having a threaded end is surrounded by a spring 24. The first bolt 20 passes through a hole 71 in mating surface 78 of the second section 70. The threaded end of the first bolt 20 is screwed into the threaded hole 61 in mating surface 68 of the first section 60. In this way, spring 24 biases the second section 70 toward the first section 60 at mating surfaces 78 and 68, respectively. As described above, first section 60 and second section 70 are separated by seal 52.

A first washer 22 also may be utilized around bolt 20. A first alignment pin 26 may also be used to ensure that the second section moves in a linear fashion as described herein and prevents the shearing of first bolt 20. First alignment pin 26 is pressed into a hole (shown in FIG. 2 but not numbered) in mating surface 68 and engages a second hole (shown in FIG. 2 but not numbered) in mating section 78 of second section 70.

The fastening assembly also includes a second bolt 30 having a threaded end. The second bolt 30 is surrounded by a spring 34. The second bolt 30 passes through a hole 73 in mating surface 79 of the second section 70. The threaded end of the first bolt 20 is screwed into the threaded hole 63 in mating surface 69 of the first section 60. In this way, spring 34 biases the second section 70 toward the first section 60 at mating surfaces 79 and 69, respectively. As described above, the first and section sections are separated by seal 52.

A second washer 32 also may be utilized around bolt 30. A second alignment pin 36 may also be used to ensure that the second section 70 moves in a linear fashion as described herein and prevents the shearing of second bolt 30. Second alignment pin 36 is pressed into a hole (shown in FIG. 2 but not numbered) in mating surface 69 and engages a second hole (shown in FIG. 2 but not numbered) in mating section 79 of second section 70. Of course, any type of fastening assembly which movably attaches first section 60 and second section 70 that is known to one of ordinary skill in the art having the benefit of this disclosure would also be acceptable.

Figure 3:
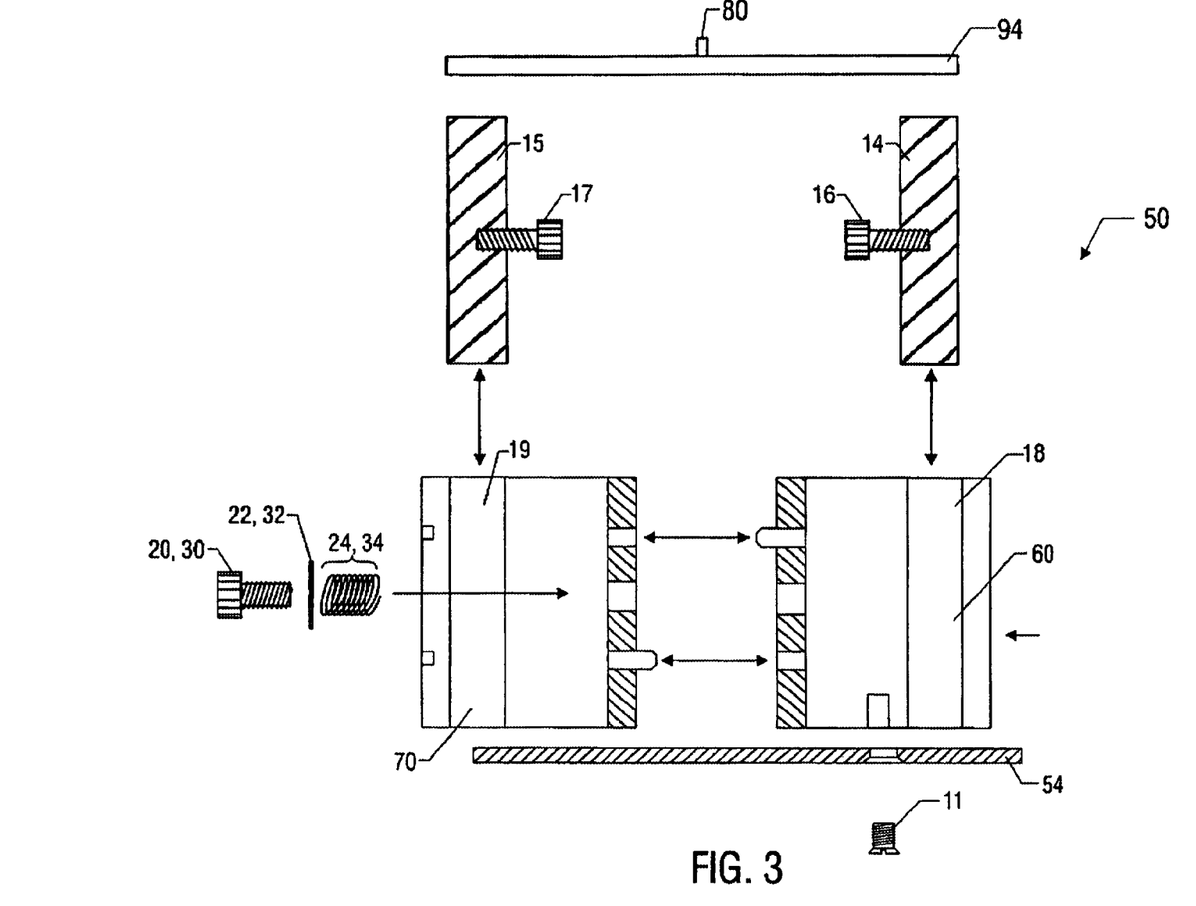
FIG. 3 shows an exploded side view of one embodiment of the present invention having anchor blocks.

Referring to FIG. 3, an exploded side view of one embodiment of the present invention is shown. The first section is fixedly attached to the base 54 via bolt 11. The second section 70 is movably attached to the first section 60 via the fastening assembly described above. The second section 70 thus rests on the base 54 and may move relative to the base in a horizontal direction, unlike the first section 60 which is fixedly attached to base 54.

The mold 50 may include a first anchor block 14 and a second anchor block 15. First and second anchor blocks 14 and 15 may be inserted into channels 18 and 19 of first and section sections 60 and 70, respectively. In this embodiment, the anchor blocks 14 and 15 have a triangular cross-section. Each anchor block 14 and 15 also includes an anchor bolt 16 and 17 respectively, to which the cement 10 may adhere, as described more fully herein.

Channels 18 and 19 secure anchor blocks 14 and 15 to preclude movement in an X or Y horizontal direction. However, channels 18 and 19 allow anchor blocks 14 and 15 to move vertically as necessary for proper operation of the mold.

A single mold 50 may be placed into the high-pressure high-temperature chamber. However, it is often desirable to have multiple cement samples in multiple molds processed under the same temperature and pressure conditions. Therefore, multiple molds 50 may be placed in a mold basket 40 as more fully described herein with respect to FIG. 4. As shown in FIGS. 1, 2, and 3, molds 50 may include at least one mounting hole for attaching the mold 50 to the basket. The mounting holes 41 may be in the mold lid 94 and in base 54.

Additionally, while not necessary, the mold 50 may have a lid 94 to cover the mold 50, once filled with cement 10, to prevent spillage thereof. Further, another sensor 80, such as a linear displacement transducer, may contact the lid 94 to measure the expansion or shrinkage of the concrete in the Z-direction, as the anchor blocks move relative to the mold 50. A seal 52 may be placed between the lid and the first and second sections 60 and 70. Seal 52 may be an O-ring, low durometer rubber seal, or TYGON tubing, for example. Further, lid 94 may be movably attached to the first and second sections 60 and 70 by a fastening assembly, identical to the movable means attaching the first and second sections. I.e., the fastening assembly may comprise a bolt surrounded by a spring, which passes through a hole in the lid, to threadedly engage in the first and second sections.

In operation, the sensor 80 is calibrated. If sensor 80 is a linear displacement transducer, the linear distance transducer 80 in conjunction with the data acquisition unit 82 is calibrated using a Vernier caliper.

A mold 50 is constructed as described above. The cement 10 to be tested is mixed and placed in mold 50. Mold 50 is then inserted into the high-pressure high-temperature chamber 90 solely, or in basket 40 stacked along with other molds 50.

Once in the high-pressure high-temperature chamber 90, the sensor may be functionally associated with the mold 50. For example, the sensor may be brought into contact with the contact location 77 of the movable second section 70 of the mold 50. The sensor 80 is in constant contact with the contact location 78, whether the cement shrinks or expands, by virtue of either a spring or electromagnetic forces of the linear displacement transducer, when used.

The high-temperature high-pressure chamber 90 is then activated to bring the contents therein to a given operating temperature and pressure simulating downhole conditions. Once the cement 10 sets, the cement 10 attaches to anchor bolts 16 and 17, when used.

Volumetric changes of the cement 10 is then monitored as follows. First section 60 is fixed to the mold base 54 and therefore does not move. If the cement 10 expands, second section 70 of mold 50 moves toward sensor 80, as the force of the cement expanding overcomes the force of springs 24 and 34 of the fastening assembly. The second section 70 moves linearly toward sensor 80, due in part to alignment pins 26 and 36, which are parallel to the axis of sensor 80. As second section 70 moves toward sensor 80, sensor 80 sends data to the data acquisition unit 82, which also stores the temperature and pressure settings of the chamber 90. Device 84 then stores the data from the acquisition unit 82 with respect to time and may display the results, if desired.

Additionally, the expansion of the cement 10 also forces anchor blocks 14 and 15 to move upwardly in channels 18 and 19 in the mold 50, as the cement 10 is attached to anchor bolts 16 and 17 once set.

In some instances, the cement 10 does not expand, but shrinks. If the cement 10 shrinks, movable second section 70 of mold 50 moves away from sensor 80, as the force of the cement shrinking overcomes seal 52. Once set, the cement 10 attaches to the anchor blocks 14 and 15. As the cement 10 shrinks, the second section 70 moves toward first section 60 and away from sensor 80. Thus, the first and second sections 60 and 70 apply a compressive force to seal 52. As the seal 52 is comprised of a resilient material such as rubber, the seal compresses.

The sensor 80 maintains contact with the second section 70, as the sensor 80 has a biasing means, such as a spring or an electromagnetic field, to ensure constant contact. The second section 70 moves linearly toward sensor 80, due in part to alignment pins 26 and 36, which are parallel to the axis of sensor 80. As second section 70 moves toward sensor 80, sensor 80 sends data to the data acquisition unit 82, which also stores the temperature and pressure settings of the chamber 90. Device 84 then stores the data from the acquisition unit 82 with respect to time and may display the results, if desired.

As second section 70 moves away from sensor 80, sensor 80 sends data to the data acquisition unit 82, which also stores the temperature and pressure settings of the chamber 90. Device 84 then stores the data from the acquisition unit 82 with respect to time and may display the results, if desired.

Figure 4:
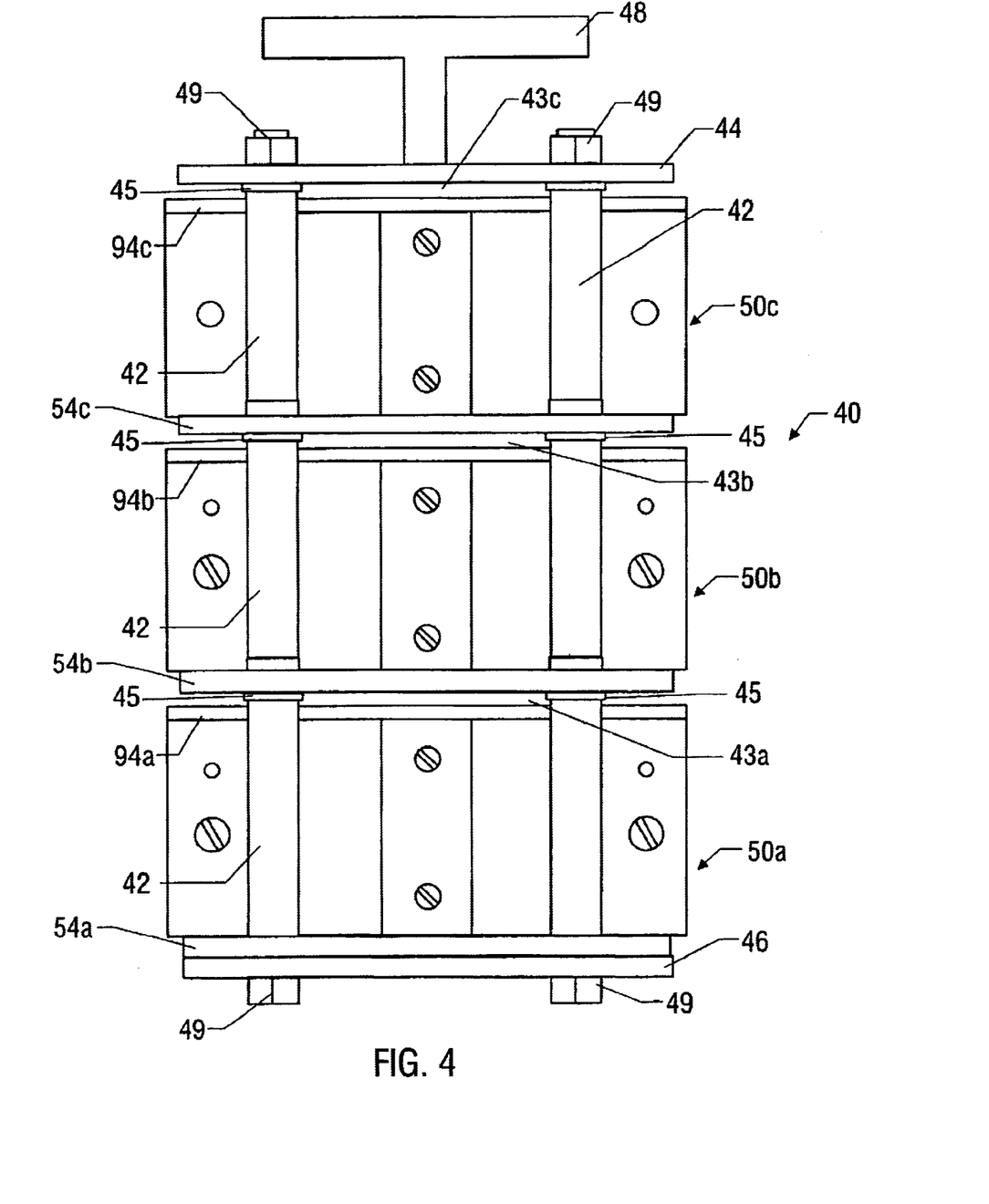
FIG. 4 shows a side view of one embodiment of the present invention having a basket.

Referring to FIG. 4, a side view of multiple (e.g. three) molds 50 placed in a basket 40 is shown. In this embodiment, basket 40 includes a bottom plate 46. In this embodiment, four mounting rods 42 are connected to the bottom plate 46. Bottom plate has mounting holes through which the mounting rods 42 may be inserted. Connected to the opposite end of the mounting rods 42 is top plate 44. Both bottom plate 46 and top plate 44 are held in place in this embodiment by being threadedly locked to mounting nuts 49.

In some embodiments, a removable handle 48 is attached to the top plate 44 to facilitate the operator's handling of the basket 40.

Multiple molds 50 may be placed between the top plate 44 and the bottom plate 46. In the embodiment shown in FIG. 4, three molds - 50a, 50b, and 50c—are shown in basket 40, although any number of molds 50 could be housed in basket 40. A first mold 50a rests on bottom plate 46a. As described above, mold 50a may include mounting holes 41 within the lid 94a and the base 54a through which mounting rods 49 are inserted.

A second mold 50b may then be stacked above the first mold 50a Again, second mold 50b includes a plurality of mounting holes in lid 94b and base 54b to accommodate the plurality of mounting rods 42. Base 54b of this second mold 50b is connected to the mounting rods 42 at a location such that the base 54b of the second mold 50b does not contact the lid 94a of the first mold 50a. Thus, gap 43a is present between the first mold 50a and second mold 50a. This is accomplished by attaching flanges 45 to the mounting rods 42 at a location above the first mold 50a such that a gap 43a is created. The second mold 50b is functionally associated with the mounting rods 42 via flanges 45. This gap allows the cement 10 in the first mold 50a to expand in the vertical direction, if needed.

A third mold 50c may then be stacked above the second mold 50b. Flanges 45 may be connected to the mounting rods 42 above the second mold 50b. The second mold 50b may be connected to the mounting rods 42 by flanges 45 such that a gap 43b exists between the second mold 50b and the third mold 50c. This gap allows the cement 10 in the second mold 50b to expand in the vertical direction, if needed.

Finally, top plate 44 of the basket 40 may be connected to the mounting rods 42 such that gap 43c exists to allow cement in the third mold 50 c to expand in the vertical direction, if needed. Top plate 44 of basket 40 may include mounting holes to accommodate the mounting rods 42. Gap 43c may be created by any number of ways, such as those known to one of ordinary skill in the art having the benefit of this disclosure. For example, flanges 45 as described above could be utilized. Alternatively, the diameter of rods 49 may be reduced at a above lid 94c such that gap 43c is created. If the mounting holes in the top plate 44 are smaller than the mounting holes 41 in the mold lid 94c, the gap 43c will be created.

Additionally, three linear displacement transducers 80 may be connected to the molds 50, one sensor per mold, to take measurements of three molds simultaneously. In this way, the device such as a computer can simultaneously process and store test data from three different cement formulations including test temperature and pressure.

Test Results

Figure 5:
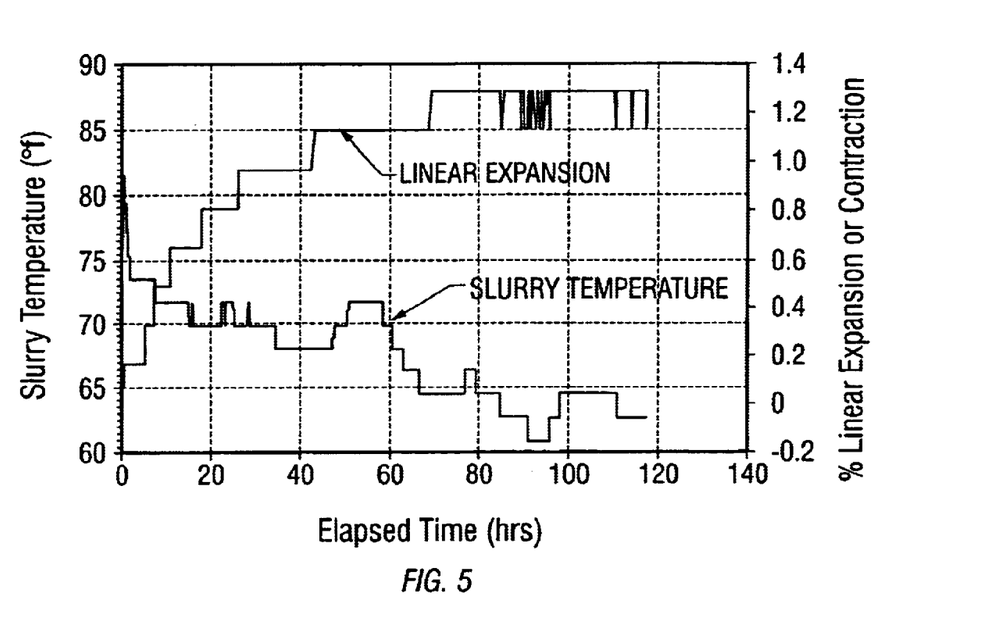
FIGS. 5–10 show experimental results of tests performed utilizing an embodiment of the present invention.
Figure 6:
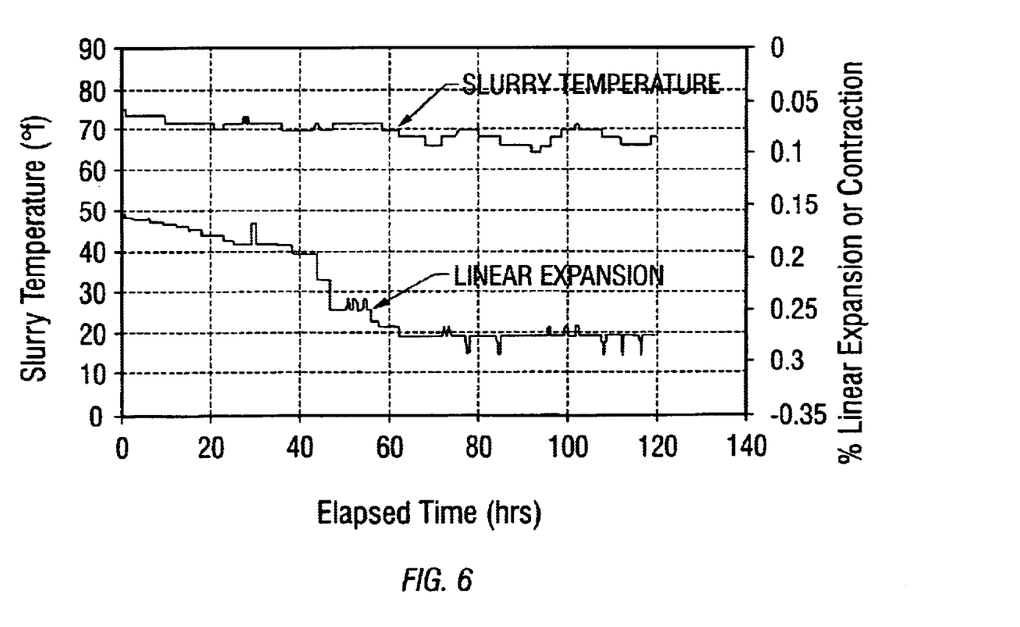

FIG. 5 and FIG. 6 demonstrate the results of expansion and contraction tests performed using the apparatus of the present invention. FIG. 5 provides expansion test data for a sample of API Class "A" Cement, which is widely known and used in the oil and gas well service industry. The cement was mixed at 15.6 PPG (pounds per gallon). An expanding cement additive available from BJ Services Company under the name EC-1 was added to the cement preparation to provide early expansion of the set cement. The EC-1 was added at an amount of 10% by weight of the cement. Linear expansion and slurry temperature data are reported. FIG. 6 provides contraction test data for API Class "A" Cement mixed at 12.5 PPG. Sodium metasilicate, an extender used to produce an economical, low density slurry was added to the cement at an amount of 2% by weight. Calcium chloride, a cement accelerator, was added at an amount of 1% by weight. Slurry temperature and percent linear contraction results were reported.

Figure 7:
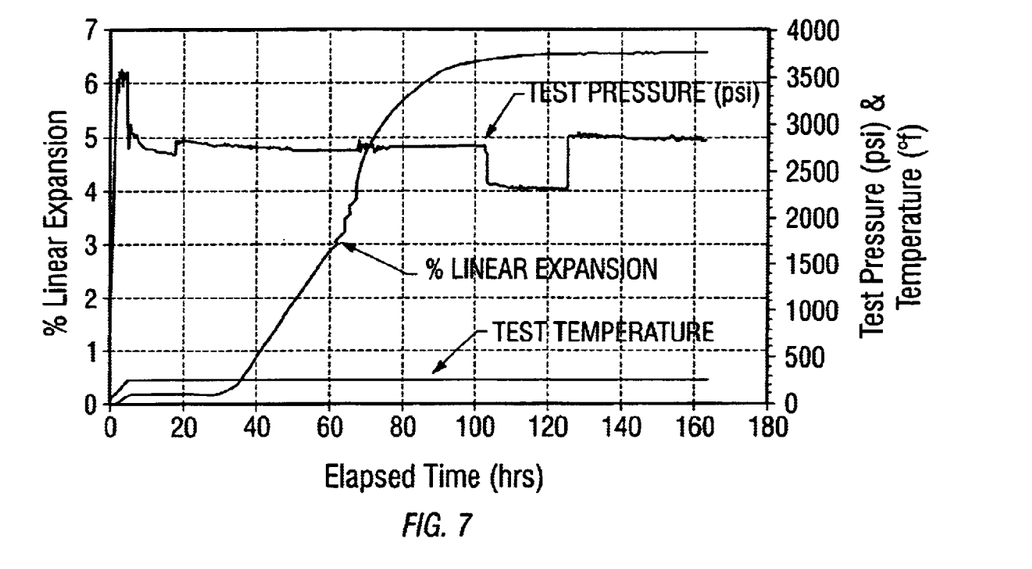

FIGS. 7, 8, 9, and 10 provide the results of additional expansion and contraction tests conducted using the invention disclosed herein. FIG. 7 provides expansion data for a cement slurry available from BJ Services Company under the name Liquid Stone®. An expanding cement additive available from BJ Services Company under the name EC-2 was added to the Liquid Stone® preparation at 7.5% by weight of the slurry. The test to measure linear expansion, test pressure and test temperature was conducted at 248° F.

Figure 8:
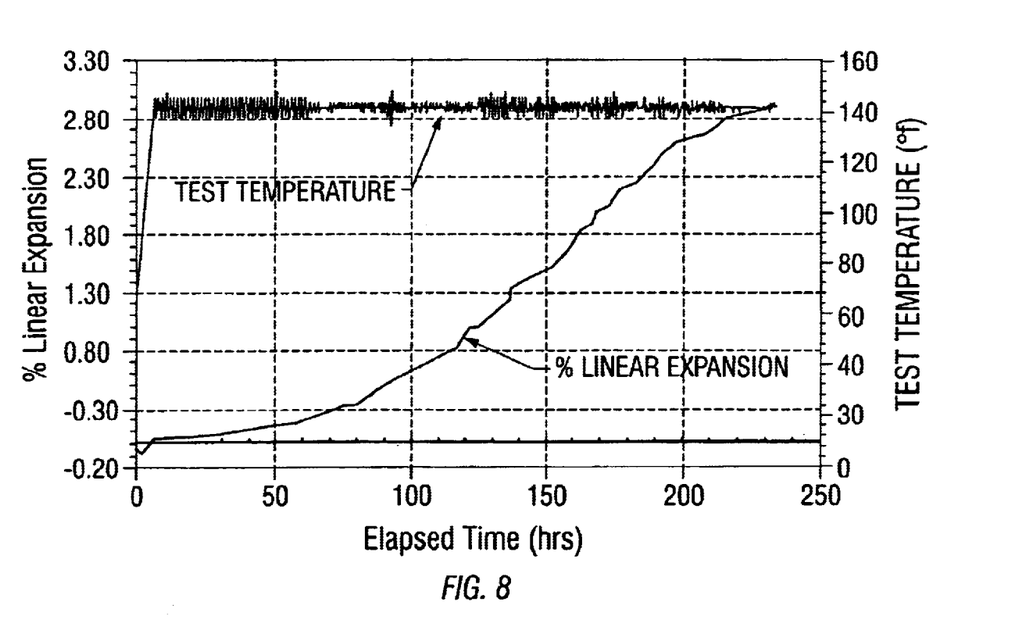

FIG. 8 provides expansion/shrinkage data for a Type I/II cement, which is widely known and used in the industry and is a construction grade cement similar to APT Class A cement. The cement slurry was prepared at 15.6 PPG. Expanding cement additive EC-1 was added at 10% by weight. A dispersant available from BJ Services Company under the name CD-32 was added at 0.4% by weight of the cement. The dispersant assists in the designing of normal density, low loss slurries that can easily be pumped in turbulent flow. The mixture yielded 1.29 cubic feet per sack of cement; and 5.57 gallons of fresh water per sack of cement were used. The test was conducted at 140° F. and 3000 psi curing pressure. Test temperature and percent linear expansion are reported.

Figure 9:
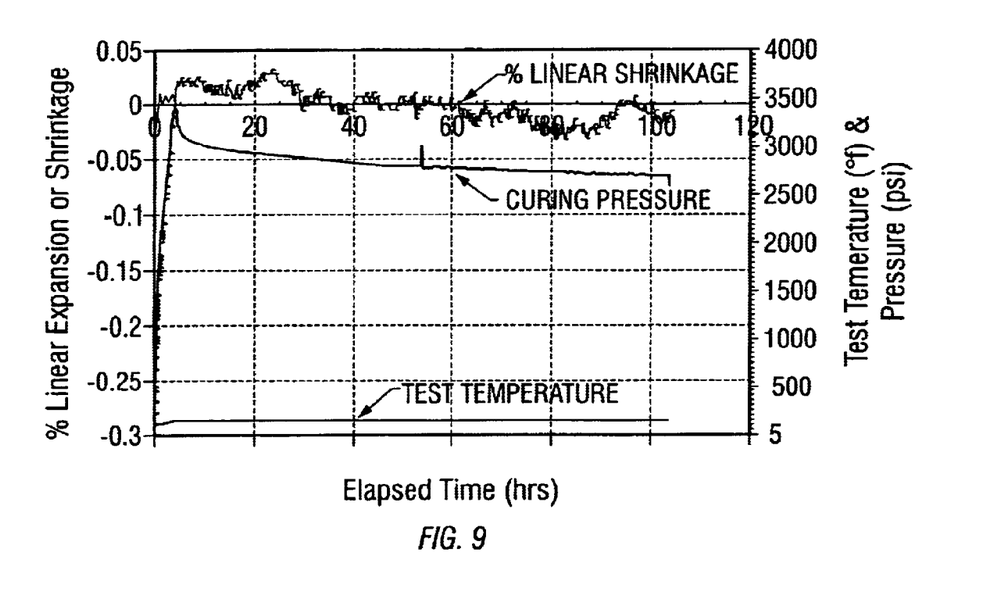

FIG. 9 provides expansion/shrinkage data for a Class G cement, an API grade cement widely known and used in the industry. The cement slurry was prepared at 15.8 PPO. The mixture yielded 1.15 cubic feet per sack of cement; and 4.99 gallons of fresh water per sack of cement were used. The test was conducted at 140° F. and 3000 psi curing pressure. Test temperature, curing pressure and percent linear expansion are reported.

Figure 10:
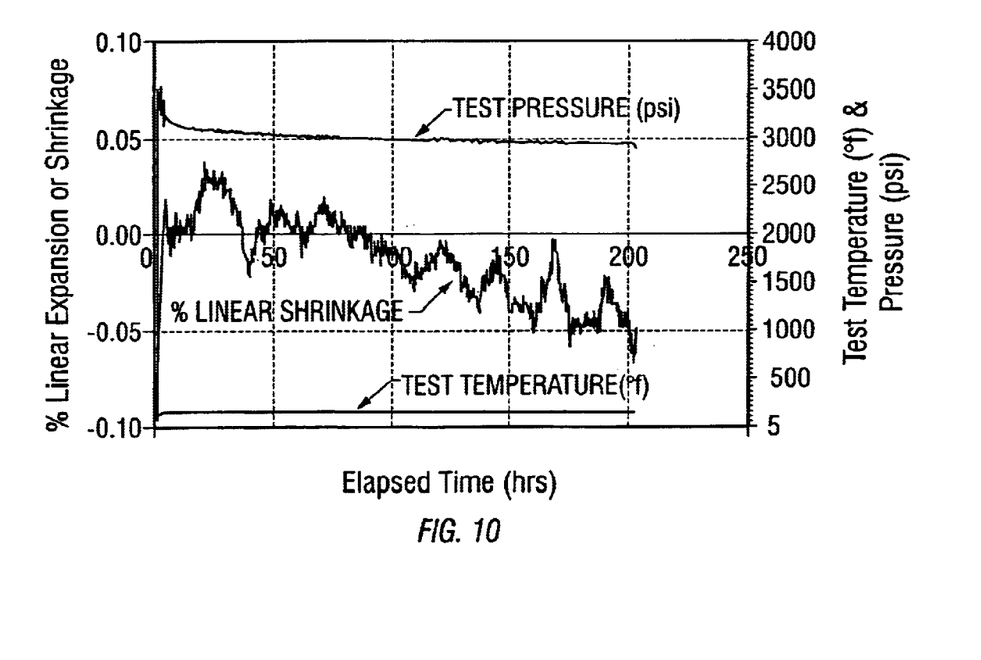

FIG. 10 provides expansion/shrinkage data for a Type I/II cement, which is widely known and used in the industry and is a construction grade cement similar to APT Class A cement. The cement slurry was prepared at 12.5 PPG.

Sodium metasilicate was added to the cement at an amount of 2% by weight. The mixture yielded 2.09 cubic feet per sack of cement; and 11.95 gallons of fresh water per sack of cement were used. The test was conducted at 140° F. and 3000 psi curing pressure. Test temperature, test temperature and percent linear expansion are reported.

Although various embodiments have been shown and described, the invention is not so limited and will be understood to include all such modifications and variation as would be apparent to one skilled in the art.

What is claimed is:

1. An apparatus for measuring volumetric changes in cement as the cement is being exposed to a given pressure and temperature in a high-pressure high-temperature chamber, comprising:
   a first section adjacent a base, the first section functionally associated with a first anchor block;
   a second section functionally associated with the first section,
      the second section adjacent the base,
      the first section, the second section, and the base defining a mold into which a measurable amount of cement may be placed, the second section functionally associated with a second anchor block; and
   a sensor adapted to measure the movement of the first and second sections relative to one another in response to volumetric changes in the cement when the cement is exposed to simulated down-hole pressures and temperatures,
      wherein the first anchor block is adapted to move with respect to the first section and the second anchor block is adapted to move with respect to the second section in response to volumetric changes of the cement when the cement is exposed to simulated down-hole pressures and temperatures.

2. The apparatus of claim 1 further comprising a seal between the first section and the second section.

3. The apparatus of claim 2 in which the seal is an O-ring.

4. The apparatus of claim 2 in which the seal is thin wall tubing.

5. The apparatus of claim 1 in which the second section is movably attached to the first section by a fastening assembly.

6. The apparatus of claim 5 in which the fastening assembly further comprises:
   a first bolt surrounded by a first spring and having a threaded end, the first bolt passing through a first hole in the second section and threadedly engaged with a first threaded hole in the first section; and
   a second bolt surrounded by a second spring and having a threaded end, the second bolt passing through a second hole in the second section and threadedly engaged with a second threaded hole in the first section, the springs adapted to bias the second section into contact with the first section.

7. The apparatus of claim 6 in which the fastening assembly further comprises two alignment pins, each alignment pin adapted to engage in holes in the first and second sections.

8. The apparatus of claim 1 in which the first section is comprised of two substantially straight sides at a first angle, each side also having a mating surface to be associated with the second section.

9. The apparatus of claim 8 in which the second section is comprised of two substantially straight sides at a second angle, each side also having a mating surface to be associated with the mating surfaces of the first section to movably attach the first and second sections.

10. The apparatus of claim 9 in which the first and second angles are 90 degrees.

11. The apparatus of claim 9 in which the sensor contacts the second section at a contact location.

12. An apparatus for measuring volumetric changes in cement as the cement is exposed to a given pressure and temperature in a high-pressure high-temperature chamber, comprising:
   a first section adjacent a base;
   a second section movably attached to the first section, the second section adjacent the base, the first section, the second section, and the base defining a mold into which a measurable amount of cement may be placed, the first section having two substantially straight sides at a first angle, each side of the first section also having a mating surface to be associated with the second section, the second section having two substantially straight sides at a second angle, each side of the second section also having a mating surface to be associated with the mating surfaces of the first section, to movably attach the first and second sections;
   a first channel in the first section adapted to receive a first anchor block having a first anchor bolt;
   a second channel in the second section adapted to receive a second anchor block having an second anchor bolt, the cement attaching to each anchor bolt once the cement is set,
      wherein the first anchor block moves with respect to the first section and the second anchor block moves with respect to the second section in response to changes in volume of the cement; and
   a sensor adapted to measure the movement of the first and second sections relative to one another in response to volumetric changes in the cement when the cement is exposed to simulated down-hole pressures and temperatures.

13. The apparatus of claim 1 in which the sensor is a linear displacement transducer.

14. The apparatus of claim 13 in which the linear displacement transducer is a spring loaded displacement transducer.

15. The apparatus of claim 13 in which the linear displacement transducer is an electromagnetic linear displacement transducer.

16. The apparatus of claim 13 in which the sensor is connected to a data acquisition unit connected to a device to store data from the sensor over time.

17. The apparatus of claim 16 in which the device is a chart recorder.

18. The apparatus of claim 16 in which the device is a computer.

19. The apparatus of claim 1 in which the first section, the second section, and the base each are comprised of brass.

20. The apparatus of claim 1 further comprising:
   a plurality of molds,
      a third section fixedly attached to a second base,
      a fourth section movably attached to the third section, the fourth section resting on the second base,
      the third section, the fourth section, and the second base defining a second of the plurality of molds into which a given amount of cement may be placed; and
   a plurality of first sensors, each first sensor functionally associated with one given mold of the plurality of molds, one of the plurality of first sensors adapted to measure the movement between the third and fourth sections of the second mold in response to volumetric changes in the cement when the cement is exposed simulated downhole conditions.

21. The apparatus of claim 20 further comprising a basket, the basket having a bottom plate connected to a top plate by a plurality of mounting rods, the plurality of molds being located between the bottom plate and the top plate.

22. The apparatus of claim 21 further comprising a handle attached to the top plate to allow the basket to be moved.

23. The apparatus of claim 21 wherein the bottom plate is connected to the mounting rods via nuts and the top plate is connected to the mounting rods via nuts.

24. The apparatus of claim 21 wherein each mold further comprises a lid having a portion defining at least one hole to accommodate the mounting rods; and a base having a portion defining at least one hole to accommodate the mounting rods.

25. The apparatus of claim 24 wherein at least one base is functionally associated with the mounting rods via a flange.

26. The apparatus of claim 25 wherein a first mold is adjacent the bottom plate of the basket and a second mold positioned substantially above the first mold in the basket, the second mold being functionally associated with the mounting rods via the flange to define a gap between the base of the second mold and the lid of the first mold, the gap allowing the cement within the first mold to expand vertically.

27. The apparatus of claim 26 wherein a third mold is positioned substantially above the second mold in the basket, the third mold being functionally associated with the mounting rods via the flanges to define a gap between the base of the third mold and the lid of the second mold, the gap allowing the cement within the second mold to expand vertically.

28. The apparatus of claim 27 wherein the top plate of the basket is positioned substantially above the third mold, the top plate being functionally associated with the rods to define a gap between the lid of the third mold and the top plate, the gap allowing the cement within the third mold to expand vertically.

29. The apparatus of claim 21 wherein a plurality of types of cement are placed into the plurality of molds.

30. The apparatus of claim 1 in which the first section has a first channel adapted to receive the first anchor block and the second section has a second channel adapted to receive the second anchor block.

31. The apparatus of claim 30 in which the first anchor block has a first anchor bolt and the second anchor block has a second anchor bolt, the cement attaching to each anchor bolt once the cement is set.

32. The apparatus of claim 31 comprising a seal between the first section and the second section, the seal adapted to compress when the cement contracts, the contraction of the cement moving second section toward the first section as the cement is attached to the first and second anchor bolts, to compress the seal.

33. The apparatus of claim 32 further comprising the first section having two substantially straight sides at a first angle, each side of the first section also having a mating surface to be associated with the second section, the second section having two substantially straight sides at a second angle, each side of the second section also having a mating surface to be associated with the mating surfaces of the first section, to movably attach the first and second sections.

34. The apparatus of claim 1 wherein the mold is also adapted to allow the cement to expand vertically.

35. The apparatus of claim 1 further comprising a lid being movably attached to the first and second section allowing the cement to expand vertically.

36. An apparatus for measuring volumetric changes in cement as the cement is exposed to a given pressure and temperature in a high-pressure high-temperature chamber, comprising:
 a first section adjacent a base;
 a second section adjacent the base and movably attached to the first section,
  the first section, the second section, and the base defining a mold into which a measurable amount of cement may be placed;
 a sensor adapted to continuously measure the movement of the first and second sections relative to one another in response to volumetric changes in the cement when the cement is exposed to simulated down-hole pressures and temperatures; and
 a lid functionally associated with the first and second sections to enclose the mold, the lid being movably attached to the first and second section allowing the cement to expand vertically.

37. The apparatus of claim 36 in which the first section, the second section, the lid, and the base each are comprised of brass.

38. The apparatus of claim 36 further comprising a seal between the lid and the first and second sections.

39. The apparatus of claim 38 further comprising a fastening assembly to movably attach the lid to the first section and second section, the fastening assembly having:
 a first bolt surrounded by a first spring and having a threaded end, the first bolt passing through a first hole in the second section and threadedly engaged with a first threaded hole in the first section; and
 a second bolt surrounded by a second spring and having a threaded end, the second bolt passing through a second hole in the second section and threadedly engaged with a second threaded hole in the first section, the springs adapted to bias the second section into contact with the first section.

40. The apparatus of claim 36 further comprising a second sensor contacting the lid adapted to measure the movement of the lid relative to the first and second sections.

41. An apparatus for measuring volumetric changes in cement as the cement is exposed to a given pressure and temperature in a high-pressure high-temperature chamber, comprising:
 a first section adjacent a base, the first section functionally associated with a first anchor block having a first bolt;
 a second section functionally associated with the first section,
  the first section, the second section, and the base defining a mold into which a measurable amount of cement may be placed, the second section adjacent the base and functionally associated with a second anchor block; and
 a sensing means for continuously measuring the movement of the first and second sections relative to one another in response to volumetric changes in the cement as the cement is exposed to simulated downhole pressures and temperatures, wherein the first anchor block is adapted to move with respect to the first section and the second anchor block is adapted to move with respect to the section when the cement is exposed to simulated down-hole pressures and temperatures.

42. The apparatus of claim 41 further comprising:
means for sealing the first section and the second section; and
means for movably attaching the second section to the first section.

43. The apparatus of claim 41 further comprising a seal between the first section and the second section.

44. The apparatus of claim 41 in which the first section is comprised of two substantially straight sides at a first angle, each side of the first section also having a mating surface to be associated with the second section, and the second section being comprised of two substantially straight sides at a second angle, each side of the second section also having a mating surface to be associated with the mating surfaces of the first section to movably attach the first and second sections.

45. An apparatus for measuring volumetric changes in cement as the cement is exposed to a given pressure and temperature in a high-pressure high-temperature chamber, comprising:
a first section adjacent a base;
a second section adjacent the base and movably attached to the first section,
the first section, the second section, and the base defining a mold into which a measurable amount of cement may be placed;
a sensor adapted to continuously measure the movement of the first and second sections relative to one another in response to volumetric changes in the cement when the cement is exposed to simulated down-hole pressure and temperatures; and
a first channel in the first section adapted to receive a first anchor block having a first anchor bolt, the cement attaching to the first anchor bolt once the cement is set; and
a second channel in the second section adapted to receive a second anchor block having a second anchor bolt, the cement attaching to the second anchor bolt once the cement is set,
wherein the first anchor block moves with respect to the first section and the second anchor block moves with respect to the second section in response to changes in volume of the cement.

46. The method of claim 45 wherein the mold is adapted to allow the cement to expand vertically.

47. The apparatus of claim 36 or 45 further comprising a seal between the first section and the second section.

48. The apparatus of claim 36 or 45 in which the second section is movably attached to the first section by a fastening assembly.

49. The apparatus of claim 36 or 45 in which the first section is comprised of two substantially straight sides at a first angle, each side of the first section also having a mating surface to be associated with the second section, and the second section being comprised of two substantially straight sides at a second angle, each side of the second section also having a mating surface to be associated with the mating surfaces of the first section to movably attach the first and second sections.

50. The apparatus of claim 12, 36, or 45 in which the first and second angles each comprise ninety degrees.

51. The apparatus of claim 12, 36, or 45 in which the sensor is a linear displacement transducer.

* * * * *